United States Patent
Pugh et al.

(10) Patent No.: US 9,833,311 B2
(45) Date of Patent: Dec. 5, 2017

(54) METHODS FOR OPHTHALMIC DEVICES INCORPORATING METASURFACE ELEMENTS

(71) Applicant: Johnson & Johnson Vision Care, Inc., Jacksonville, FL (US)

(72) Inventors: Randall B. Pugh, Jacksonville, FL (US); Frederick A. Flitsch, New Windsor, NY (US)

(73) Assignee: Johnson & Johnson Vision Care, Inc., Jacksonville, FL (US)

(*) Notice: Subject to any disclaimer, the term of this patent is extended or adjusted under 35 U.S.C. 154(b) by 942 days.

(21) Appl. No.: 13/833,716

(22) Filed: Mar. 15, 2013

(65) Prior Publication Data

US 2014/0277436 A1    Sep. 18, 2014

(51) Int. Cl.
| | | |
|---|---|---|
| B29D 11/00 | (2006.01) | |
| A61F 2/16 | (2006.01) | |
| G02C 7/04 | (2006.01) | |
| G02C 7/10 | (2006.01) | |
| G02B 1/00 | (2006.01) | |
| G02C 7/08 | (2006.01) | |

(52) U.S. Cl.
CPC ...... *A61F 2/1624* (2013.01); *B29D 11/00807* (2013.01); *G02B 1/002* (2013.01); *G02C 7/04* (2013.01); *G02C 7/085* (2013.01); *G02C 7/10* (2013.01); *G02C 7/101* (2013.01); *Y10T 29/49982* (2015.01)

(58) Field of Classification Search
CPC ...... A61F 2/1624; A61F 2/147; A61F 2/3094; A61F 2/30767; A61F 2002/3084; G02C 7/085; G02C 7/04; G02C 7/046; G02C 7/049; G02C 7/101; B29D 11/00807; B29D 11/00038; B29D 11/00048; B29D 11/00057; G02B 1/002; Y10T 29/49885; Y10T 29/4998; Y10T 29/49982
USPC .......................................................... 264/1.7
See application file for complete search history.

(56) References Cited

U.S. PATENT DOCUMENTS

| | | | | |
|---|---|---|---|---|
| 7,704,684 B2* | 4/2010 | Rogers | ...................... | B82B 3/00 430/325 |
| 8,300,294 B2* | 10/2012 | Wu | ........................ | G02B 1/007 359/240 |
| 8,318,055 B2* | 11/2012 | Widman et al. | ............. | 264/1.38 |
| 8,882,264 B2* | 11/2014 | Bradley | ................... | G02C 7/02 351/159.05 |

(Continued)

FOREIGN PATENT DOCUMENTS

| | | |
|---|---|---|
| JP | 2012-185944 | 9/2012 |
| KR | 20080111658 A | 12/2008 |

(Continued)

OTHER PUBLICATIONS

EP Search Report EP 14 15 974424 Date of Completion Jan. 7, 2015.

(Continued)

*Primary Examiner* — Sarang Afzali

(57) ABSTRACT

This invention describes Ophthalmic Devices with media inserts that have nanostructured Metasurface elements upon or within them. In some embodiments passive ophthalmic devices of various kinds may be formed. Methods and devices for active ophthalmic devices based on Metasurface structures may also be formed.

17 Claims, 13 Drawing Sheets

(56) References Cited

U.S. PATENT DOCUMENTS

| | | | |
|---|---|---|---|
| 2004/0079195 | A1 | 4/2004 | Perry et al. |
| 2006/0262398 | A1 | 11/2006 | Sangu et al. |
| 2009/0051059 | A1* | 2/2009 | Widman et al. ............ 264/1.36 |
| 2009/0051834 | A1* | 2/2009 | Cottier ........................... 349/14 |
| 2009/0068374 | A1 | 3/2009 | Shin |
| 2009/0213459 | A1* | 8/2009 | Amirparviz ................... 359/465 |
| 2010/0079724 | A1* | 4/2010 | Pugh ............... B29D 11/00009 351/159.75 |
| 2011/0069377 | A1 | 3/2011 | Wu et al. |
| 2012/0120365 | A1* | 5/2012 | Legerton et al. ........ 351/159.02 |
| 2012/0234453 | A1 | 9/2012 | Pugh et al. |

FOREIGN PATENT DOCUMENTS

| | | |
|---|---|---|
| WO | WO 2005072078 A2 | 8/2005 |
| WO | WO 2005072078 A3 | 1/2006 |
| WO | WO 2008013780 A2 | 1/2008 |
| WO | WO 2010/039645 A1 | 4/2010 |
| WO | WO 2011035230 A2 | 3/2011 |
| WO | WO 2013/033591 A1 | 3/2013 |

OTHER PUBLICATIONS

Singapore Search Report Application No. 10201400585T Date of submission of the request Sep. 29, 2014 Date of the actual completion of the Search Jan. 16, 2015; Date the report was received from the Singapore agent Mar. 10, 2015.

EP Search Report EP 14 15 974424 Dated Jun. 24, 2014.

Romain Blanchard et al: "Modeling nanoscale V-shaped antennas for the design of optical phased arrays". Physical Review B. vol. 85. No. 15, Apr. 1, 2012 • XP055124817. ISSN: 1098-0121. D01: 10.1103/PhysRevB. 85.155457.

Andrea Di Falco et al: Flexible metamaterials at visible wavelengths; New Journal of Physics, Institute of Physics Publishing, Bristol, GB, vol. 12, No. 11, Nov. 4, 2010, p. 113006, XP020200092, ISSN: 1367-2638, D01: 10.1088/1367-2630/12/11/113006.

EP Communication for Application 14 159 744.4-1562 Ref P063495EP Date Jul. 27 2016 ; Date sent to Johnson & Johnson Aug. 25 2016.

* cited by examiner

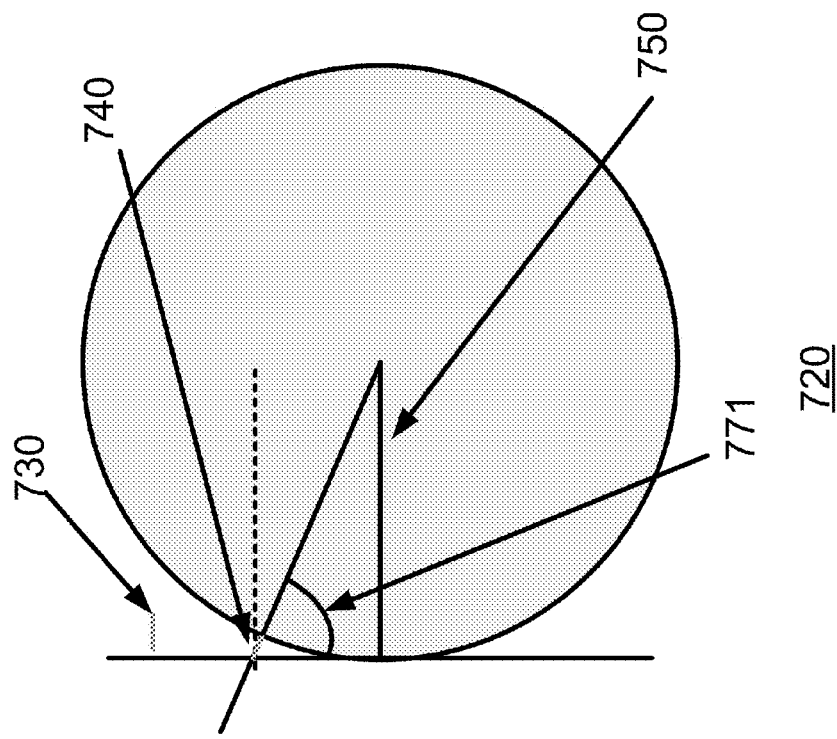
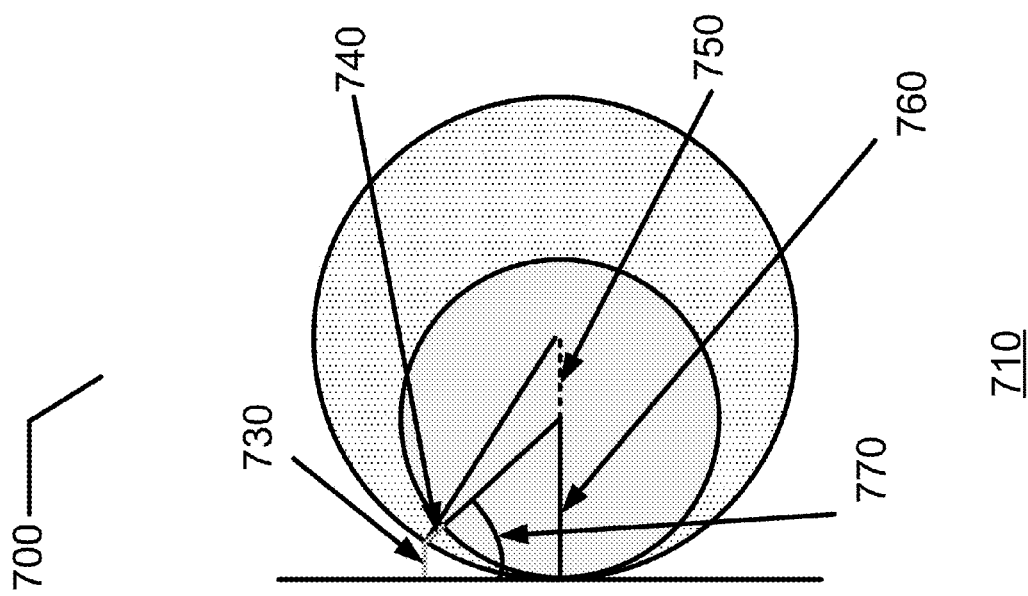
FIG. 7 ns may be used. In some
METHODS FOR OPHTHALMIC DEVICES INCORPORATING METASURFACE ELEMENTS

FIELD OF USE

This invention describes Ophthalmic Devices with media inserts and Lenses that have Metasurface elements upon or within them.

BACKGROUND

Traditionally, an ophthalmic device, such as a contact lens, an intraocular lens, or a punctal plug, included a biocompatible device with a corrective, cosmetic, or therapeutic quality. A contact lens, for example, may provide one or more of vision correcting functionality, cosmetic enhancement, and therapeutic effects. Each function is provided by a physical characteristic of the lens. A design incorporating a refractive quality into a lens may provide a vision corrective function. A pigment incorporated into the lens may provide a cosmetic enhancement. An active agent incorporated into a lens may provide a therapeutic functionality. Such physical characteristics are accomplished without the lens entering into an energized state. A punctal plug has traditionally been a passive device.

Novel ophthalmic devices based on energized and non-energized ophthalmic inserts have recently been described. These devices may use the energization function to power active optical components.

Recently, it has been demonstrated that unique flat lenses may be formed by the fabrication of specialized surface structure having Nanoscale metallic features arrayed on the surface. Various designs may be made through control of the Nanoscale feature's unit cell structure designs.

It may be useful to define ophthalmic devices to result from the incorporation of Nanoscale structures.

SUMMARY

Accordingly, the present invention includes a Media Insert with included Nanoscale metallic features that comprise a Metasurface. The Metasurface may be a repeating pattern of sub-wavelength sized features to a particular wavelength of light. The interaction of the sub-wavelength sized features may interact with the light and alter the phase characteristics of reemitted light from the features. The features in this sense may also be considered Nanoscale antennas. There may be numerous methods to form Nanoscale metallic features on an insert and these inserts may be encapsulated in a lens skirt of ophthalmic material to form ophthalmic devices.

In some embodiments, an insert device may be defined by forming Nanoscale metallic features into a periodic pattern across at least a portion of a surface of an insert device. The periodic pattern may have a length factor for the periodicity that is approximately equal or less than various wavelengths of visible light. In some embodiments, the design of the shape and size factors of the metallic features may be determined based on modeling a desired phase characteristic of the Nanoscale features. Light that is incident upon the Metasurface elements may emerge with altered phase characteristics and this may be modeled. The design may be an ab-initio modeling process where the nature of the structure, layout, feature location and other factors and the desired effect on light are used in a self-consistent model. Alternatively iterative modeling based on trial designs with adjustments based on previous results may be used. In some embodiments, the desired lens characteristics of the Nanoscale metallic surface may have a radially symmetric focusing lens characteristic. Models may generate desired phase characteristics that have the radial symmetry and a focal characteristic of the effect of the collection of elements. When the insert is formed to have a three dimensional and curved surface as opposed to a flat surface, there may be estimation protocols that may be useful to transform the resulting lens characteristics of an Ophthalmic device with the Metasurface elements into a model of the Ophthalmic device in three dimensional space and the Metasurface as a equivalent flat space. There may be estimates to the effective focal characteristics of the Metasurface that may result in design parameters. The process may be used with the iterative modeling process as mentioned above.

In some embodiments, the modeling processes may occur through the use of software based algorithms for which parameters may be provided by a user and which may be run on computing systems. The parameters that a user provides may be based upon theoretical requirements. In other cases, Ophthalmic practitioners may measure the Ophthalmic characteristics and corrective needs of a patient and formulate these needs into a set of parameters for the modeling system. The computer systems may provide numerical output in some embodiments or provide spatially designed elements as arrays of design data points.

In some embodiments, preferably where the wavelength of the light is in a visible spectrum, the metallic features may have small surface area dimensions. As an example, the Metasurface features may have surface area dimensions that are 10,000 $nm^2$ or less. There might be much diversity in the periodic nature of the placement of the Metasurface elements. They might be deployed in rectilinear, polar or radial patterns, or other periodic patterns. The spacing of nearest neighbors may be related to the desired wavelengths of light to be interacted with by the elements. In some embodiments, this spacing may be less then or approximately equal to the early red spectrum that may occur in the visible spectrum. In some embodiments, the spacing or periodicity may be less then or approximately equal to 700 nm.

The insert may be enveloped in a lens skirt. A lens skirt may be made of materials that are typically employed in the production of contact lenses, such as for example hydrogels. Molded into the ophthalmic skirt may be stabilization features that may be useful to orient the lens within the eye. These features may be of particular use for Metasurface lens elements that have high order correction aspects to them where the correction aspects are not radially symmetric. Various designs of inserts may be employed which may fit into the resulting ophthalmic device. The overall shape of the surface of the insert that has the Metasurface elements upon it may be convex in nature or alternatively concave in nature. Other shapes that may be formed into inserts for ophthalmic devices may also comprise art within the scope of this disclosure.

Active or non-static embodiments of the Metasurface elements may also be produced. In some embodiments, metallic layers may be formed into features that may be used under the influence of electrical energy to form or enhance the activity of Metasurface elements. The periodicity and shape aspects of the actively formed structures may be similar to the discussions in the preceding sections. Electrowetting on Dielectric (EWOD) principles may be useful in some embodiments. One of the immiscible fluids in an EWOD device may contain metallic nanospheres or metallic nanorods. In some embodiments, the nanospheres or nanorods may have surface modifications to enhance their preference to one or another of the EWOD fluids. In some embodiments, the surface modification may be carried out by the chemical attachment of ligand molecules to the Nanoscale metallic components. The surface of the insert where Metasurface elements will be actively formed may have regions that have a preferred surface free energy to interact differentially with the EWOD fluids. In some embodiments, the resting state of the EWOD regions may define a condition where the fluid containing the nanospheres, nanorods or other shaped metallic constituents may be diffuse in space. By the application, of an electric field in the EWOD device the regional preference may be switched resulting in an accumulation of the fluid containing Nanoscale metallic constituents into shapes that comprise Metasurface elements.

Contact lenses may be formed which comprise inserts with three-dimensional shapes to them where at least portions of the surfaces of the inserts may have static or active Metasurface elements upon them where the Metasurface elements have a lens effect. Some embodiments with active Metasurface elements may comprise components that act with the phenomena of Electrowetting on Dielectrics. Within fluids of EWOD cells may be Nanoscale components that in some cases may comprise nanospheres or nanorods. Modification of the surface of the Nanoscale components in the fluid may be performed in various manners and may include the chemical attachment of molecules to the surfaces of the Nanoscale components to change their preference to one or more of the Electrowetting on Dielectric fluids. Embodiments with active Metasurface elements upon them may respond to an electric field that may be controlled by other components located in the insert or within the ophthalmic device. In some embodiments a variable focus contact lens may result from an electrically controllable formation of active surface Metasurface elements.

DESCRIPTION OF THE DRAWINGS

FIG. 7 Illustrates a phase characteristic estimation useful to model the lens.

DETAILED DESCRIPTION OF THE INVENTION

Figure 1:
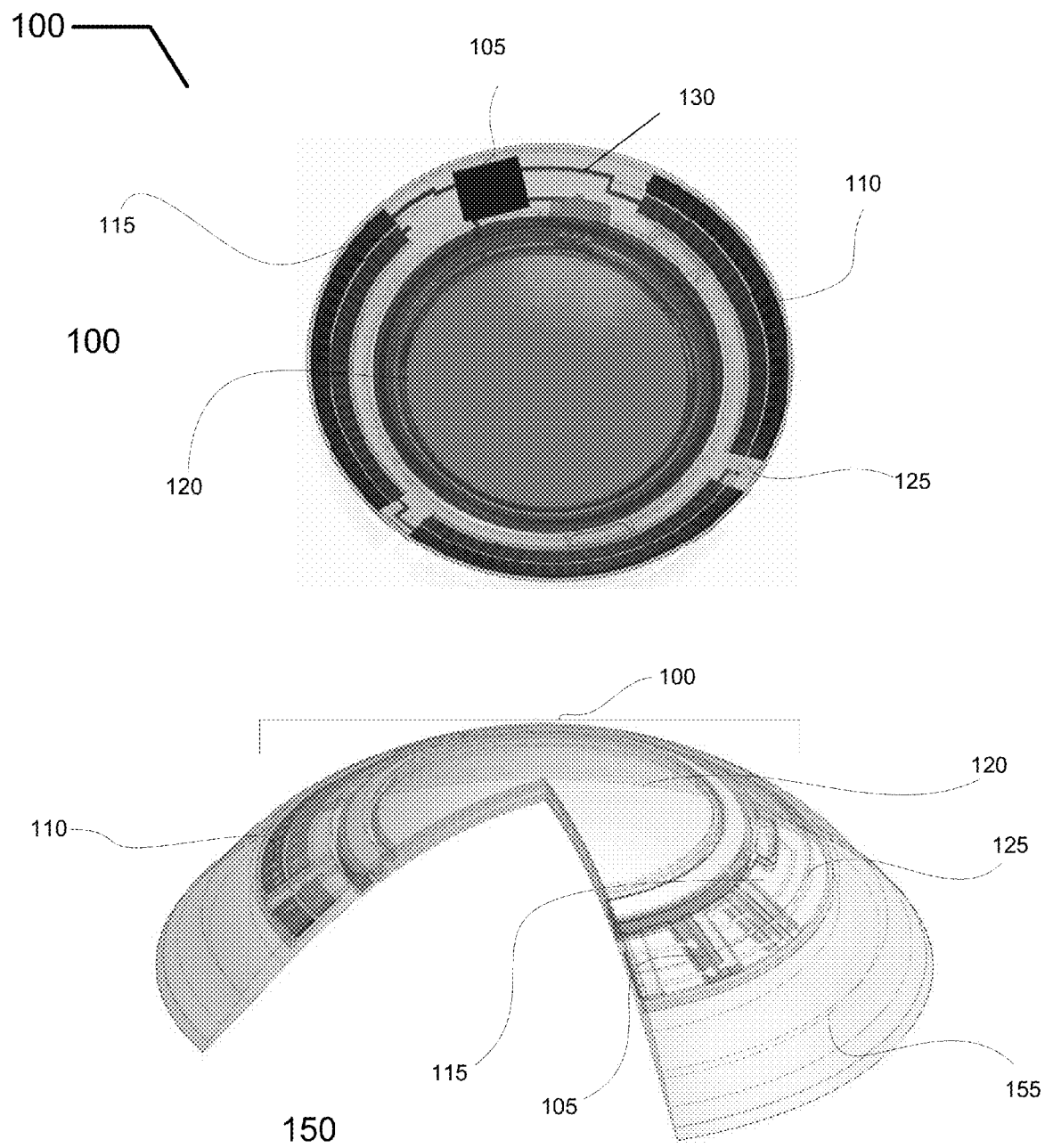
FIG. 1 illustrates an exemplary embodiment of a Media Insert for an energized ophthalmic device and an exemplary embodiment of an energized Ophthalmic Device.

The present invention relates to an ophthalmic device having Metasurface components that may affect changes in electromagnetic radiation in the environment of the eye. In the following sections detailed descriptions of embodiments of the invention will be given. The description of both preferred and alternative embodiments are exemplary embodiments only, and it is understood that to those skilled in the art that variations, modifications and alterations may be apparent. It is therefore to be understood that said exemplary embodiments do not limit the scope of the underlying invention.

GLOSSARY

In this description and claims directed to the presented invention, various terms may be used for which the following definitions will apply:

Energized: as used herein refers to the state of being able to supply electrical current to or to have electrical energy stored within.

Energy: as used herein refers to the capacity of a physical system to do work. Many uses within this invention may relate to the said capacity being able to perform electrical actions in doing work.

Energy Source: as used herein refers to a device or layer that is capable of supplying Energy or placing a logical or electrical device in an Energized state.

Energy Harvester: as used herein refers to a device capable of extracting energy from the environment and converting it to electrical energy.

Functionalized: as used herein refers to making a layer or device able to perform a function including for example, energization, activation, or control.

Leakage: as used herein refers to unwanted loss of energy.

Lens or Ophthalmic Device: as used herein refers to any device that resides in or on the eye. These devices may provide optical correction, may be cosmetic, or may provide functionality unrelated to the eye. For example, the term lens may refer to a contact lens, intraocular lens, overlay lens, ocular insert, optical insert, or other similar device through which vision is corrected or modified, or through which eye physiology is cosmetically enhanced (e.g. iris color) without impeding vision. Alternatively, the Lens may provide non-optic functions such as, for example, monitoring glucose or administrating medicine. In some embodiments, the preferred lenses of the invention are soft contact lenses are made from silicone elastomers or hydrogels, which include, for example, silicone hydrogels, and fluorohydrogels.

Lens-forming mixture or Reactive Mixture or Reactive Monomer Mixture (RMM): as used herein refers to a monomer or prepolymer material that may be cured and crosslinked or crosslinked to form an ophthalmic lens. Various embodiments may include lens-forming mixtures with one or more additives such as, for example, UV blockers, tints, photoinitiators or catalysts, and other additives one might desire in an ophthalmic lenses such as, contact or intraocular lenses.

Lens-forming Surface: as used herein refers to a surface that is used to mold a lens. In some embodiments, any such surface can have an optical quality surface finish, which indicates that it is sufficiently smooth and formed so that a lens surface fashioned by the polymerization of a lens forming material in contact with the molding surface is optically acceptable. Further, in some embodiments, the lens-forming surface can have a geometry that is necessary to impart to the lens surface the desired optical characteristics, including without limitation, spherical, aspherical and cylinder power, wave front aberration correction, corneal topography correction and the like as well as any combinations thereof.

Lithium Ion Cell: as used herein refers to an electrochemical cell where Lithium ions move through the cell to generate electrical energy. This electrochemical cell, typically called a battery, may be reenergized or recharged in its typical forms.

Media Insert: as used herein refers to an encapsulated insert that will be included in an energized ophthalmic device. The energization elements and circuitry may be incorporated in the Media Insert. The Media Insert defines the primary purpose of the energized ophthalmic device. For example, in embodiments where the energized ophthalmic device allows the user to adjust the optic power, the Media Insert may include energization elements that control a liquid meniscus portion in the Optical Zone. Alternatively, a Media Insert may be annular so that the Optical Zone is void of material. In such embodiments, the energized function of the Lens may not be optic quality but may be, for example, monitoring glucose or administering medicine.

Metasurface: as used herein refers to man-made combinations of Nanoscaled features arrayed with periodicity. The combinations result in useful characteristics that are distinct from natural structures. In many embodiments herein, the interaction of the features with light, particularly in a visible spectrum allow for lens devices to be constructed.

Mold: as used herein refers to a rigid or semi-rigid object that may be used to form lenses from uncured formulations. Some preferred molds include two mold parts forming a front curve mold part and a back curve mold part.

Nanoscale: as used herein refers to an element that has a feature or features that has or have at least one dimension that is smaller than approximately 1 micron; thus its dimensionality for that at least one dimension may be referred to in nanometers.

Operating Mode: as used herein refers to a high current draw state where the current over a circuit allows the device to perform its primary energized function.

Optical Zone: as used herein refers to an area of an ophthalmic lens through which a wearer of the ophthalmic lens sees.

Power: as used herein refers to work done or energy transferred per unit of time.

Rechargeable or Re-energizable: as used herein refers to a capability of being restored to a state with higher capacity to do work. Many uses within this invention may relate to the capability of being restored with the ability to flow electrical current at a certain rate and for a certain, reestablished time period.

Reenergize or Recharge: as used herein refers to restoring to a state with higher capacity to do work. Many uses within this invention may relate to restoring a device to the capability to flow electrical current at a certain rate and for a certain, reestablished time period.

Reference: as use herein refers to a circuit which produces an, ideally, fixed and stable voltage or current output suitable for use in other circuits. A reference may be derived from a bandgap, may be compensated for temperature, supply, and process variation, and may be tailored specifically to a particular application-specific integrated circuit (ASIC).

Released from a Mold: as used herein refers to a lens is either completely separated from the mold, or is only loosely attached so that it may be removed with mild agitation or pushed off with a swab.

Reset Function: as used herein refers to a self-triggering algorithmic mechanism to set a circuit to a specific predetermined state, including, for example, logic state or an energization state. A Reset Function may include, for example, a power-on reset circuit, which may work in conjunction with the Switching Mechanism to ensure proper bring-up of the chip, both on initial connection to the power source and on wakeup from Storage Mode.

Sleep Mode or Standby Mode: as used herein refers to a low current draw state of an energized device after the Switching Mechanism has been closed that allows for energy conservation when Operating Mode is not required.

Stacked: as used herein means to place at least two component layers in proximity to each other such that at least a portion of one surface of one of the layers contacts a first surface of a second layer. In some embodiments, a film, whether for adhesion or other functions may reside between the two layers that are in contact with each other through said film.

Stacked Integrated Component Devices or SIC Devices: as used herein refers to the products of packaging technologies that assemble thin layers of substrates that may contain electrical and electromechanical devices into operative-integrated devices by means of stacking at least a portion of each layer upon each other. The layers may comprise component devices of various types, materials, shapes, and sizes. Furthermore, the layers may be made of various device production technologies to fit and assume various contours.

Storage Mode: as used herein refers to a state of a system comprising electronic components where a power source is supplying or is required to supply a minimal designed load current. This term is not interchangeable with Standby Mode.

Substrate Insert: as used herein refers to a formable or rigid substrate capable of supporting an Energy Source within an ophthalmic lens. In some embodiments, the Substrate insert also supports one or more components.

Switching Mechanism: as used herein refers to a component integrated with the circuit providing various levels of resistance that may be responsive to an outside stimulus, which is independent of the ophthalmic device.

Three-dimensional: as used herein refers to a shape or surface that is essentially not planar.

Energized Ophthalmic Device

Proceeding to FIG. 1, an exemplary embodiment of a Media Insert 100 for an energized ophthalmic device and a corresponding energized ophthalmic device 150 are illustrated. The Media Insert 100 may comprise an Optical Zone 120 that may or may not be functional to provide vision correction. Where the energized function of the ophthalmic device is unrelated to vision, the Optical Zone 120 of the Media Insert 100 may be void of material. In some embodiments, the Media Insert 100 may include a portion not in the Optical Zone 120 comprising a substrate 115 incorporated with energization elements 110 and electronic components 105. There may be numerous embodiments relating to including Metasurface elements into ophthalmic devices; however many may define surface portions within the Optical Zone 120 upon which Metasurface elements are deployed.

In some embodiments, a power source 110, which may be, for example, a battery, and a load 105, which may be, for example, a semiconductor die, may be attached to the substrate 115. Conductive traces 125 and 130 may electrically interconnect the electronic components 105 and the energization elements 110. The Media Insert 100 may be fully encapsulated to protect and contain the energization elements, traces, and electronic components. In some embodiments, the encapsulating material may be semipermeable, for example, to prevent specific substances, such as water, from entering the Media Insert 100 and to allow specific substances, such as ambient gasses or the byproducts of reactions within energization elements, to penetrate or escape from the Media Insert 100.

In some embodiments, the Media Insert 100 may be included in an ophthalmic device 150, which may comprise a polymeric biocompatible material. The ophthalmic device 150 may include a rigid center, soft skirt design wherein a central rigid optical element comprises the Media Insert 100. In some specific embodiments, the Media Insert 100 may be in direct contact with the atmosphere and the corneal surface on respective anterior and posterior surfaces, or alternatively, the Media Insert 100 may be encapsulated in the ophthalmic device 150. The periphery 155 of the ophthalmic Lens 150 may be a soft skirt material, including, for example, a hydrogel material.

The infrastructure of the media insert 100 and the ophthalmic device 150 may provide an environment for numerous embodiments involving nanostructured elements to form Metasurfaces. Some of these embodiments may involve purely passive function of the ophthalmic device, where for example, the Metasurface component performs optical effects relating to vision correction for example. Other embodiments, may involve the ophthalmic device having active functions where once again the Metasurface components themselves perform a passive function. In addition, in still further embodiments the Metasurface components may themselves be part of the active function of the ophthalmic device.

Figure 2:
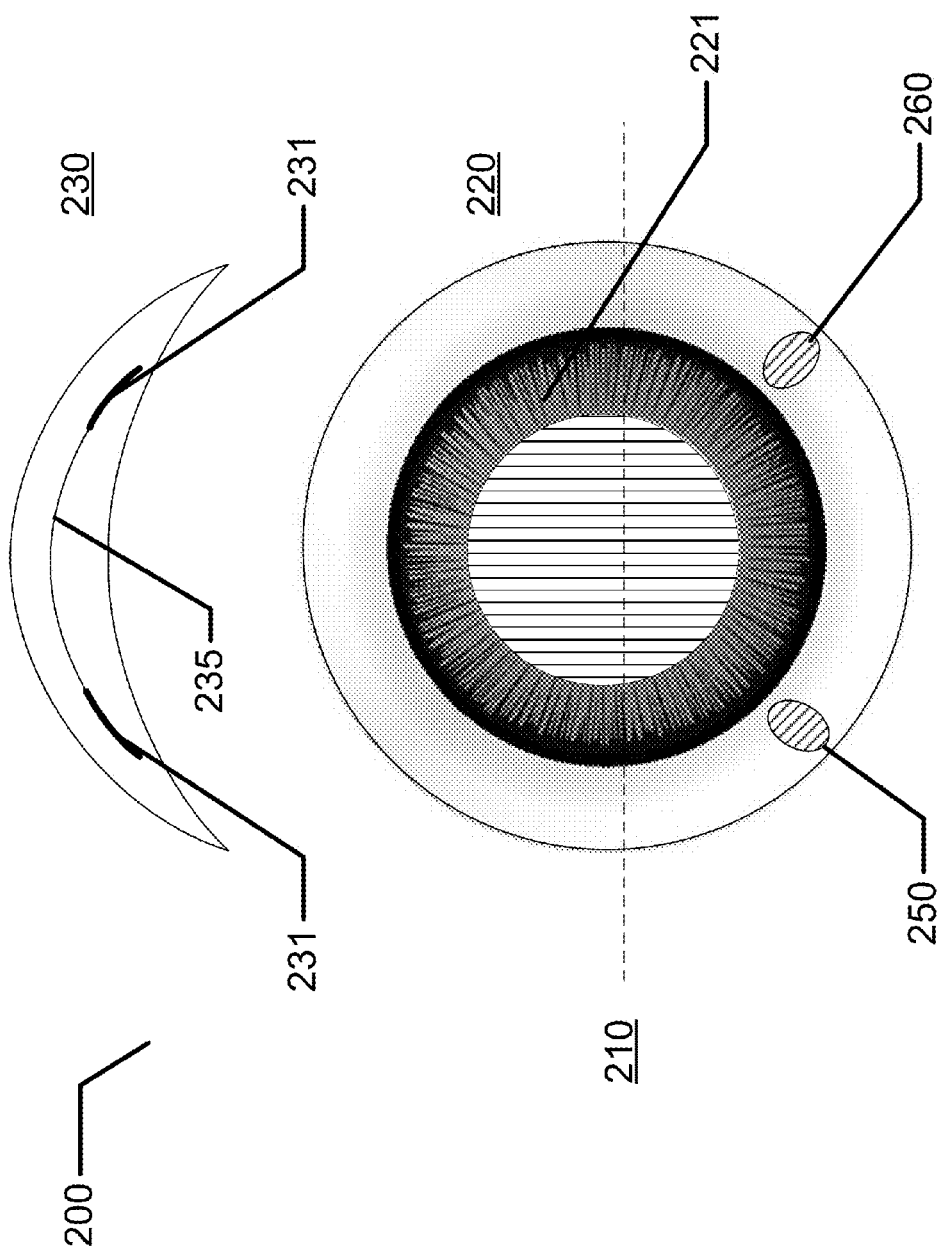
FIG. 2 illustrates an exemplary contact lens with various features including an incorporated single piece insert that may be useful for implementing aspects of the art herein.

Proceeding to FIG. 2, item 200 a depiction of an exemplary single piece insert may be illustrated in cross section. In FIG. 2, the ophthalmic device, 220, may have a cross sectional representation, 230, which represents a cross section through the location represented by line 210. In an exemplary embodiment, the optic zone of the ophthalmic device 220 may include a polarizing element, which may be represented in the cross section as item 235. Upon the surface of item 235 may be nanostructured elements to form the Metasurface. In other embodiments, item 235 may solely represent a surface that has the Metasurface elements thereupon. Item 235 may represent a three dimensionally formed substrate which is attached to other insert forming pieces to form an insert.

As well, outside the optic zone of the device there may be printed patterns placed on the single piece insert as shown by item 221 and in cross section as items 231. In some embodiments, the insert piece may simply comprise the Metasurface components at 235 and an optionally printed region at 231.

As shown in the cross section, the single piece insert piece 235 may have a three dimensional shape. For example, the piece may assume the three dimensionally curved shape by thermoforming a thin sheet material that may start in a planar format. The Metasurface elements may be added to the sheet either before or after this thermoforming is performed.

In some embodiments, there may be a requirement for orientation of the ophthalmic lens within the ocular environment. Items 250 and 260 may represent stabilization zone features that can aid in orienting the formed ophthalmic lens upon a user's eye. In addition, in some embodiments the use of stabilization features upon the single piece insert may allow for its orientation relative to the molded stabilization features. The ability to orient may be particularly important for placements of Metasurface features that are not radially symmetric in nature, as would be case for a pattern that may correct second order and higher aberrations in vision.

Figure 3:
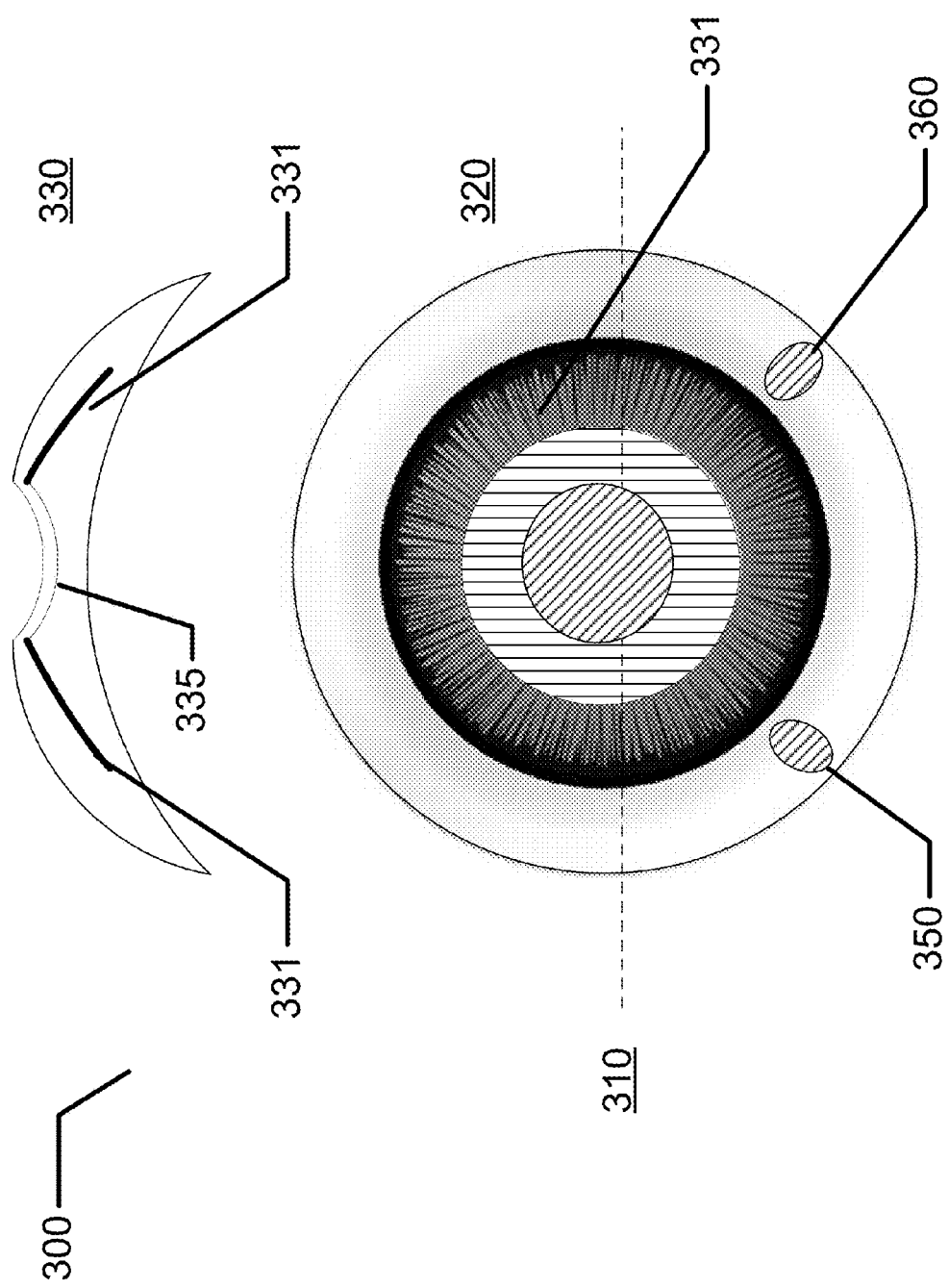
FIG. 3 illustrates an exemplary alternative embodiment to that demonstrated in FIG. 2.

Proceeding to FIG. 3, item 300 a variation of the exemplary single piece insert shown in FIG. 2, may be illustrated in cross section. In FIG. 3, the ophthalmic device, 320, may have a cross sectional representation, 330, which represents a cross section through the location represented by line 310. In an exemplary embodiment, the optic zone of the ophthalmic device 320 may include a portion, not necessarily shown to scale in the figure, where the surface shape is concave to incident radiation as opposed to the convex orientation. This may allow for embodiments, where instead of adjusting focusing aspects of the ophthalmic lens the Metasurface elements may adjust divergent aspects of the lens surface. Upon this concave surface of item 335 may be nanostructured elements to form the Metasurface. As well, outside the optic zone of the device there may be printed patterns placed on the single piece insert as shown by item 331. In some embodiments, the insert piece may simply comprise the Metasurface components at 335 and an optionally printed region at 331. For the same motivations as the embodiment in FIG. 2, there may be alignment features or stabilization zones incorporated into ophthalmic device as shown as items 350 and 360, and there may be patterns printed upon the insert as features 331.

Figure 4:
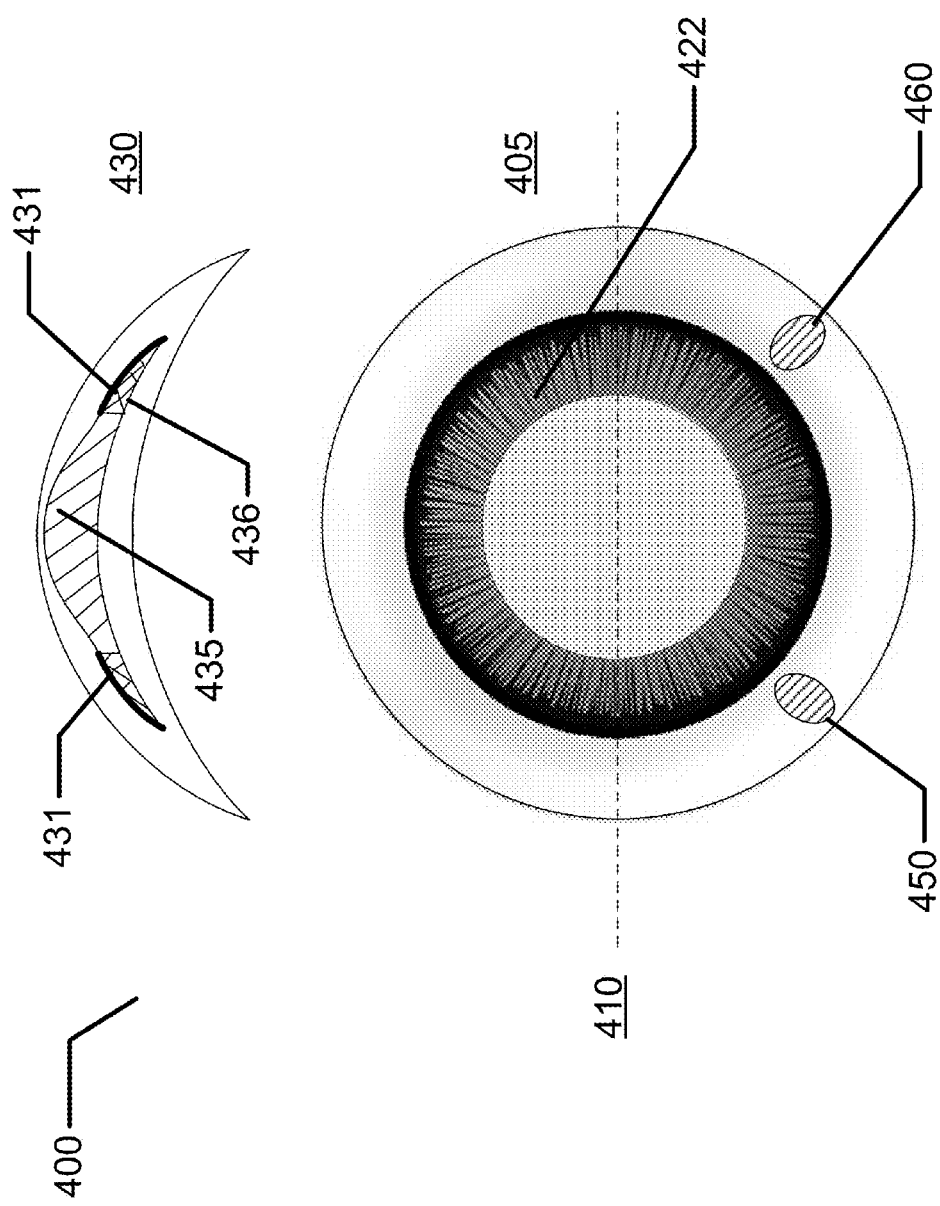
FIG. 4 illustrates an exemplary contact lens with various features including an incorporated multipiece insert that may be useful for implementing aspects of the art herein.

Proceeding to FIG. 4, item 400 additional embodiments where multi-piece inserts may be used to form ophthalmic devices may be observed. In item 405 a multi-piece insert 422 may include an active element in the optic zone. The figure depicts a cross sectional representation 430 across line 410. For exemplary purposes, the ophthalmic lens also includes printed features as item 431, which may also be represented in cross section as item 431. In addition, the exemplary lens may include stabilization features 450 and 460.

Multi-piece inserts may also be useful for embodiments with annular shapes where there is no insert material in the optical zone. With Metasurfaces, a modification of this type of annular insert may be made where a two piece annular shape is found in regions depicted as item 436 whereas a single piece of the insert may be located in the optical zone and support the Metasurface elements.

An exemplary embodiment of a multipiece insert may include a meniscus based active lens element at item 435 between the two insert pieces. The meniscus lens may actively change focal characteristics when a battery-powered circuit applies electric potential across parts of the meniscus lens. Metasurface elements may also be included upon one of the multipiece surfaces. In a non-limiting example, the inclusion of passive Metasurface focusing elements upon the surface of an active meniscus lens may allow for the adjustment of optical characteristics for higher order corrective aspects of the lens.

The multipiece insert may include an active Nanoscale Metasurface embodiment as well. In subsequent sessions discussion is found for an embodiment that actively forms Metasurface elements within the region between the two insert pieces at item 435. In some such embodiments, the optical zone may have preferred orientations relative to the use's eyes. The methods used to form such a Metasurface including ophthalmic device may allow for registered alignment of the various components of the lens to the stabilization elements 450 and 460. These elements will then maintain an established orientation of the lens relative to the user's eyes.

Metasurface Lens Elements

Figure 5:
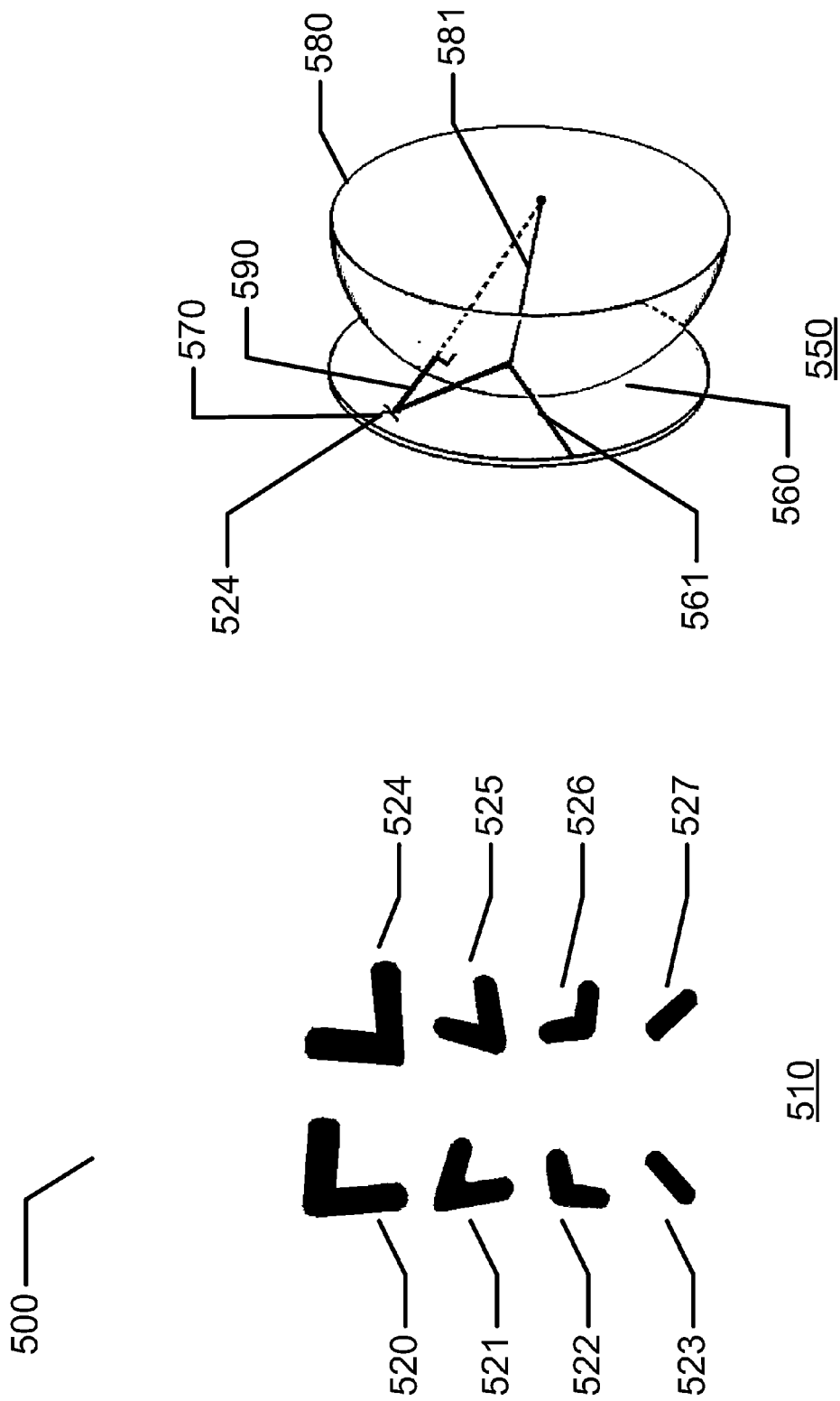
FIG. 5 illustrates aspects of prior art related to a flat Metasurface element based lens and to designing the Metasurface elements with a hyperboloidal phase profile to function as a lens.

Proceeding to FIG. 5, item 500 aspects of prior art implementations of flat surface based lens devices based on the phase altering interaction of light with Nanoscale metallic elements is displayed. In some implementation of flat surface lenses, small metallic features may be defined upon the flat surface in a design that interacts with light upon the surface of the flat lens. In items 520 through 527 a set of designs of a functional lens are depicted. The features of 510 comprise the unit cell of Metasurface elements that are deployed across the flat surface in such a manner to form a lens.

In an exemplary embodiment, the lens is optimized for wavelength around 1.5 microns, a common communication electromagnetic wavelength out of the visual spectrum. In other embodiments, optimization may occur for wavelengths in the visual spectrum. The unit cell varies from item 520 to 523. The length of the components ranges from 180 to 85 nanometers in length, and as can be observed there is an angle between linear elements of that length that ranges from approximately 90 angstroms to zero. The thickness of the metal comprising the Metasurface devices may be approximately 50 nanometers and devices may be separated from each other by spacing ranging from 750 nanometers down to 200 nanometers. When closer than 200 nanometers, the Metasurface components may tend to "communicate" with each other and alter the properties of neighboring devices. In the demonstration of functional devices, the number of unit cell components was made in four discrete steps although in practice the number of different component designs may be significantly more. The various parameters relate to demonstrated practice for a certain wavelength range. Variation of the design aspects of the Metasurface elements in 510 including their thickness and lengths may be useful in tuning the Metasurface elements to different wavelength ranges.

The depicted elements and the parameters mentioned above relate to design aspects used to create a flat lens where the phase alteration of the Metasurface antenna elements is used to model a hyperboloidal radial phase distribution 590 that results in a lens. In 550, the important elements relating to estimating the desired phase characteristic of an element placed upon the flat lens 560 may be found. The lens 560 may have a radius as shown as item 561. The modeled lens may have a focal length characteristic shown as item 581. The modeled phase characteristics of a Metasurface element, for example 524, at position 570 which may be represented as position (x,y), is such that the Phase shift characteristic represented by item 590 is proportional to the projection of the location vector upon the spherical model surface 580. That will result in the desired lens function with the desired focal characteristic 581. It can be demonstrated that for such parametric relationships that such projection for the phase shift PS(x,y) will follow the relationship of $$PS(x, y) \cong \frac{2\pi}{\lambda}(\sqrt{(x^2 + y^2) + f^2} - f) \quad (1)$$

Where PS(x,y) represents the desired phase shift of a point x,y on the flat lens, and λ represents the wavelength of the light, and f represents the focal characteristic of the lens desired. In a polar coordinate system the phase shift PS(r, Θ) is $$PS(r, \Theta) \cong \frac{2\pi}{\lambda}(\sqrt{r^2 + f^2} - f) \quad (2)$$

It may be apparent that incorporation of flat lenses of this type may create novel ophthalmic devices. In an intraocular device, a flat focusing plane may be possible. Utilizing designs of this kind within intraocular devices may be practical for adjusting focal characteristics in a static sense. Alternatively, the active element embodiments discussed in three dimensionally shaped devices in coming sections may likewise have relevance for flat lens type intraocular embodiments.

Figure 6:
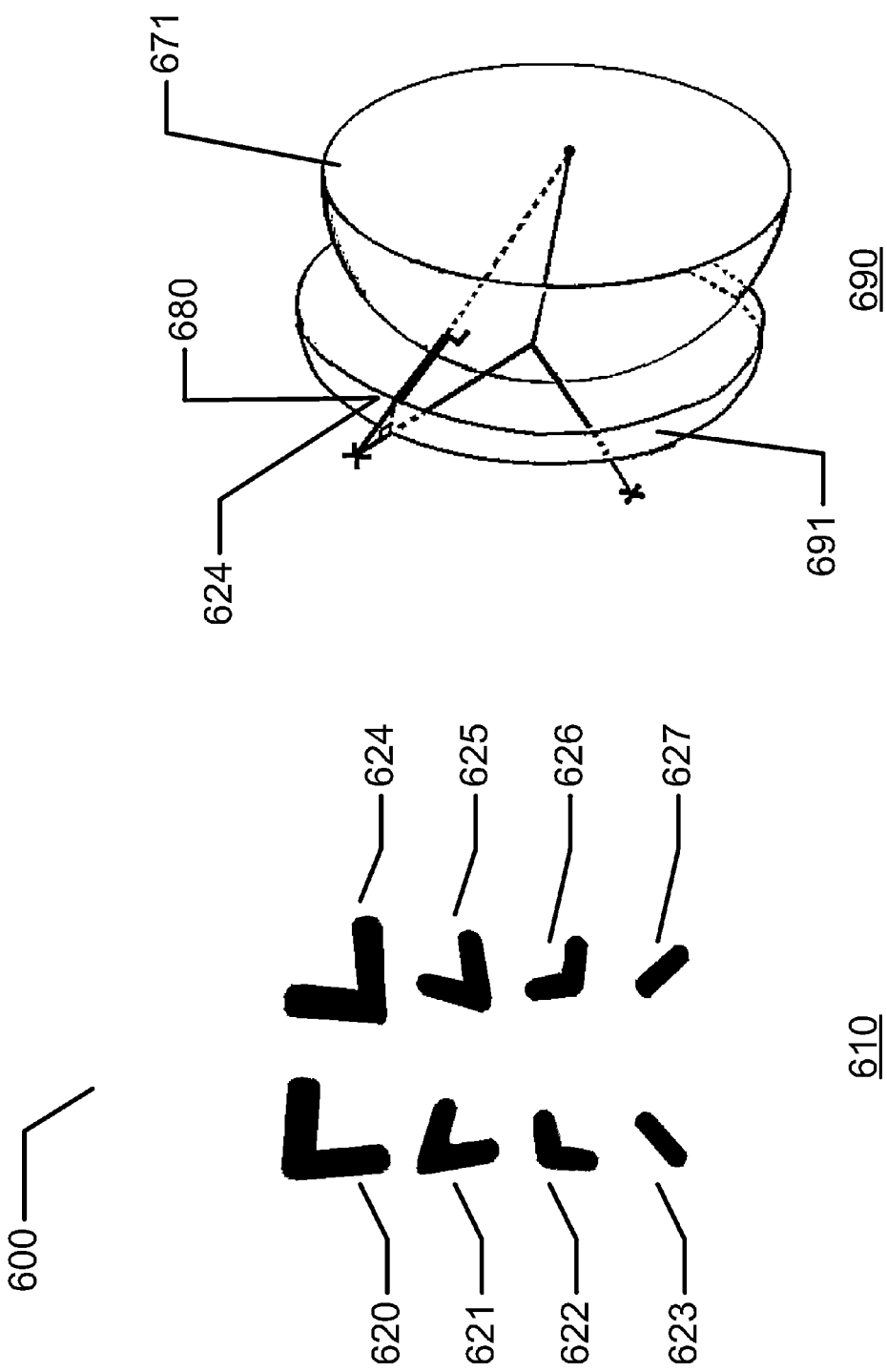
FIG. 6 illustrates changes to the nanostructure modeling based on three dimensional lens substrates rather than flat substrates.

Proceeding to FIG. 6, item 600 the resulting model for such a lens condition where the surface is not flat may be depicted. It may be practical to use similar unit cell designs for the Metasurface Nanoscale elements as shown in 610 as items 620-627. Where the design aspects of the elements such as their thickness, angle of features and lengths may be related to the desired central wavelength of focus and to the calculated phase shift characteristics desired.

It may be apparent that switching from a flat lens to a curved lens may introduce additional complexity in modeling the device. The physical phase characteristics to an incident plane wave based on the curved surface may introduce a first component of phase aspects of the device. In addition, now Metasurface elements may reside upon a globally curved surface that will change the angular orientation of the antenna feature in space. Furthermore, as the surface curves, the straight lined distance between nanoshaped Metasurface elements and each other may be different from the distance along the surface itself between elements.

There may be some reasonable estimation that may allow for estimated lens design parameters. For example, to a first order it may be possible to treat the phase characteristics of the curved surface, introducing a phase alteration of the plane wave interaction with the surface, and the phase altering characteristics of the Metasurface antenna elements as independent. Thus to model the design parameters of the Metasurface antenna, it may be sufficient to consider the desired change of the phase due to the Metasurface antenna independent of the other phase shift by subtracting that phase shift from the overall phase shift of the three dimensionally formed lens device.

In estimation, since the Nanoscale Metasurface antennas are so small it may be a good estimate to model them as points. Although, there may be differences in how the plane wave interacts with a tilted Nanoscale Metasurface element, it may still be acceptable to ignore the impact by estimating the small device as a point that is not affected by the distortion that curving the lens surface may introduce.

In addition, in another estimation the spacing between elements in the design may be estimated based on the distance between the elements in a non-curved space. In practice, the density of Nanoscale elements may affect the efficiency of the focusing device and a curved implementation may decrease the density that Nanoscale elements may be placed at. Nevertheless, devices may still be created with first order effects within the estimate that the curved space does not limit the design density of Nanoscale elements.

The effect of curved space may be observed in the depiction of FIG. 6, item 690. A spherical model surface may be depicted as item 671. A curved surface may be depicted as item 691 where a Nanoscale Metasurface element such as item 624 may be located at a point on the surface (x', y', z') at point 680. The resulting impact on the phase length characteristics may be observed as the shortened phase length 691. The equations for estimating the phase shift may become equations whose dependence is three dimensional and represented by PS(x,y,z) or alternatively in a cylindrical coordinate system as PS(r, Θ, h).

Applying the various estimates mentioned, a method to apply the desired overall lens characteristics to a curved lens surface with Metasurface elements may be discussed in relationship to FIG. 7, item 700. In item 710, a graphical depiction of the curved surface with Metasurface elements may be found. The combinational phase characteristics of the lens shape as item 730 and then the Metasurface component as item 740 may be depicted. In an exemplary case where the Metasurface and the physical curved surface are radially symmetric and focusing, a difference in focal length of the combined phase shifts may be understood as item 750, where item 760 may represent the resulting lens focal characteristic as item 760. It may be a reasonable estimate to focus on the relative construction angle of the two different independent focal characteristics where 770 may represent the angle of the Metasurface impacted focal characteristic on top of the physical curved lens surface focal characteristic.

Continuing with estimates, in 720 the case resulting if you decouple the phase shift characteristics of the curved ophthalmic lens device from the Metasurface device may be depicted. If the three dimensional impact of the total phase impact of the curved lens with Metasurface elements is estimated to come entirely from the curved device phase characteristic, then it may be estimated that by subtracting the PSlens(x,y,z) phase characteristics across the lens surface you can transform the desired Metasurface modeling condition to again match that of a flat lens as discussed in reference to FIG. 6. This may be the equivalent of the cylindrical coordinate system having a representation where the height parameter—h is set to zero. If the resulting transformation is estimated to occur by maintaining the focal length contributions that may be modeled by maintaining the relative angles of the focal length characteristics as shown by item 771 then a new estimated focal characteristic for a transformed phase space flat lens model may be represented as item 750. Then the design aspects for such Metasurface elements may be calculated in the same manner as mentioned relating to FIG. 6, and equation 1, 2 where the "f" is now an estimated effective focal length from item 750. In practice more sophisticated wavefront modeling systems may be used to rigorously calculated the desired phase characteristics of arbitrary three dimensional curved surfaces and the resulting desired phase characteristics of Nanoscale Metasurface elements deployed thereon. For, making devices consistent with the art herein, with estimated optical characteristics, the global estimates may be applied.

In the estimated case where the cylindrical coordinates may be compressed to a polar coordinate relationship by the subtraction of the three dimensional characteristics of the physical lens substrate then the polar coordinate phase representation may again be $$PS(r, \Theta) \cong \frac{2\pi}{\lambda}\left(\sqrt{r^2 + f'^2} - f'\right) \quad (3)$$

Furthermore, the modeling of the design parameters of the individual Metasurface elements can be carried out with sophisticated modeling protocols as for example Finite Difference Time-Dependent (FTDT) electromagnetic simulations. These simulations may be computationally intensive if carried out on full three dimensionally deployed nanosurface elements but possible. Alternatively the estimates discussed previously may provide an alternative to generate results that may be iteratively corrected through production, measurement and refined estimation cycles.

Figure 8:
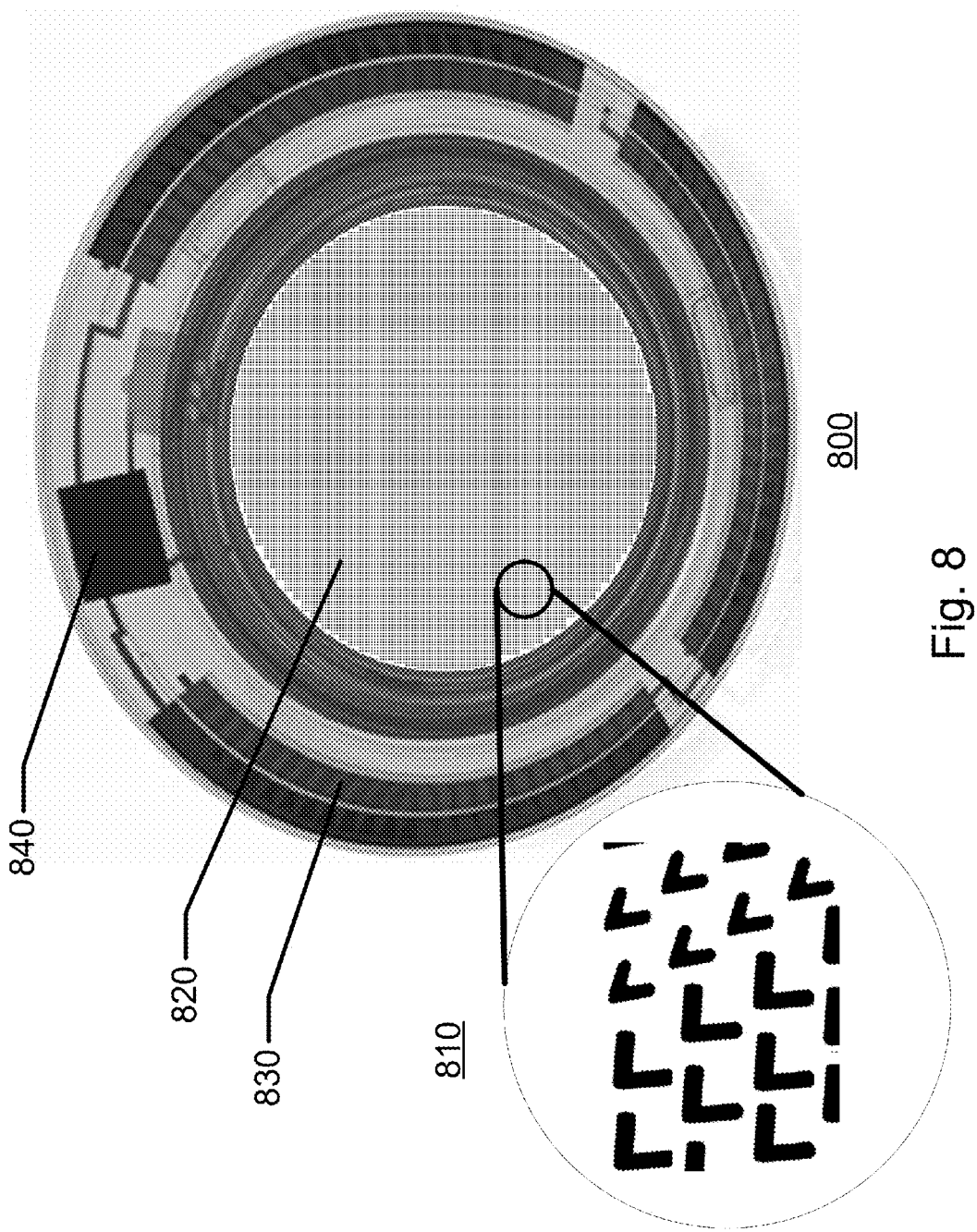
FIG. 8 Illustrates an exemplary media insert comprising active elements and Metasurface elements.

Proceeding to FIG. 8, item 800, an exemplary embodiment of some of the concepts may be found. Item 800 may represent an ophthalmic insert device that may be included within an ophthalmic lens in some embodiments, or represent an ophthalmic device on its own. The example includes energization elements 830 that energize control circuitry 840 that may comprise an integrated circuit. The integrated circuit as well as other components may control other active components within the device. In a non-limiting example, in the active zone may be a meniscus-based lens capable of adjusting the optical power when light proceeds through the device. Overlying this device in the optical zone, at 820 may be the Metasurface elements. In the magnified inset of 810, the Metasurface elements may be observed. These elements may be designed to provide a static optical correction that in combination with the active change in optical power of the underlying lens element may provide novel function.

Figure 9:
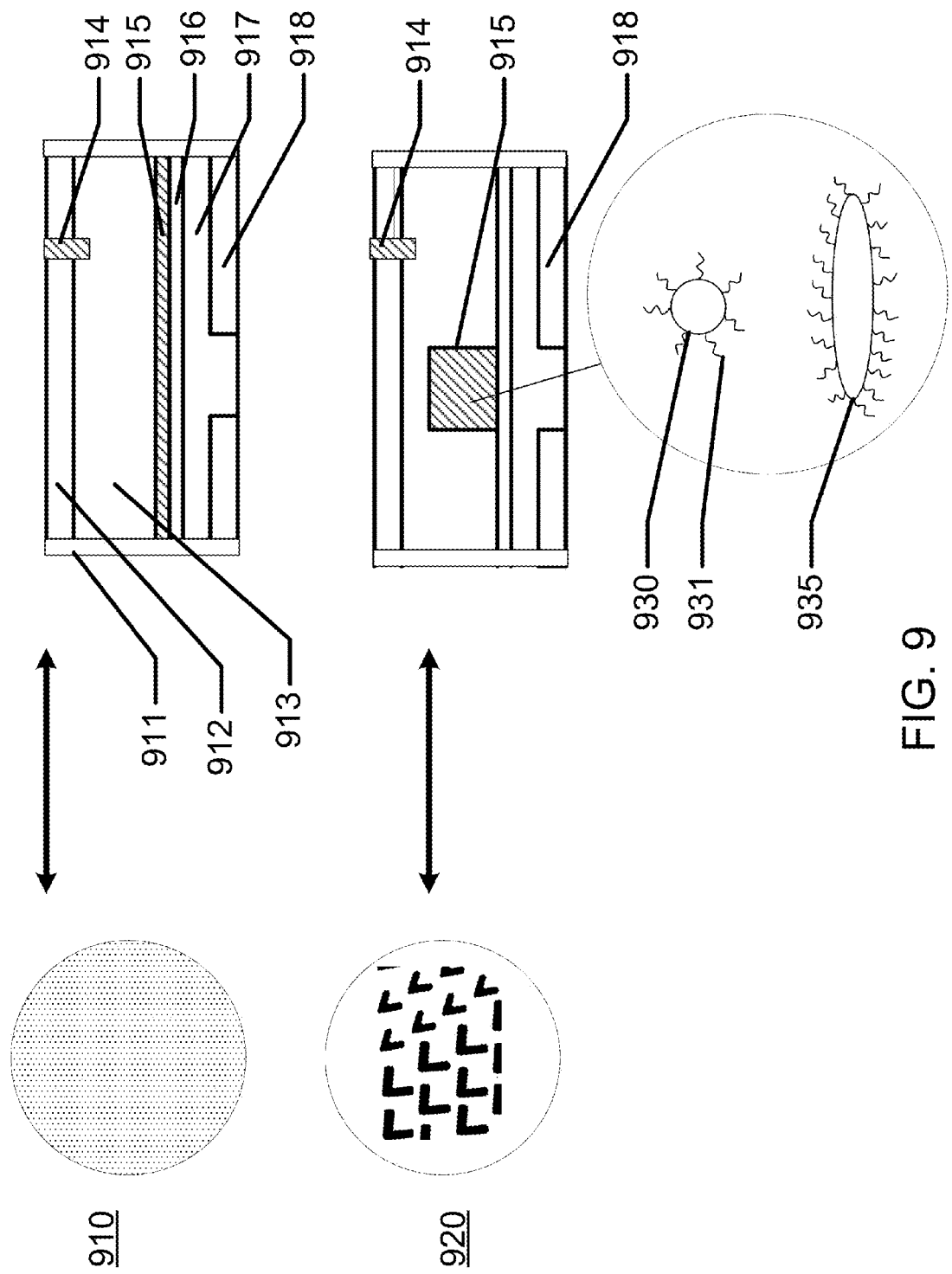
FIG. 9 Illustrates an exemplary active ophthalmic device with structures that introduce Metasurface elements upon activation.

In some embodiments, as shown in FIG. 9, the Metasurface elements may be defined in active manners as well. The exemplary meniscus lens discussed in item 800 may typically employ the technique of Electrowetting on dielectrics (EWOD). The technique acts on combinations of liquids by changing the surface free energy of surfaces near the liquids. Combinations of immiscible liquids, where one liquid, for example is a polar liquid like an aqueous solution, and the other liquid is a non polar liquid like an oil may be effective for EWOD devices. The technique may be used to create active creation of Metasurface elements. In item 910, a combination of EWOD type liquids without an applied electrical field across an active surface may result in a diffuse lens effect without regularly defined Metasurface elements. The highlight of 910 depicts a diffuse location of elements. These elements may be found in the fluid layer identified as 915. In the inset, the fluid layer 915 may be comprised of solvated components. In some embodiments these components may be metallic nanospheres such as shown by item 930 or metallic nanorods as shown as item 935. The metallic components may be comprised of Gold, Silver, Platinum or other elements that can form nanosized components.

The surface of the nanocomponents may be coated with chemicals that impart a surface energy to the nanosized component. These coated chemicals may establish a preference to certain fluid types or away from certain fluid types. The ligand molecules, 931 shown attached to the nanospheres 930 may in some embodiments make the nanospheres hydrophilic in nature or alternatively hydrophobic. If the nanospheres were hydrophilic they may be preferentially located in the aqueous component of the EWOD liquid mixture. When the first liquid contains the nanosized components, like 915 in the depiction, the other component 913 may be devoid of them. Then the fluids may be contained in microscale structures that are surrounded by a top 912, side structures 911 and a surface layer 916 upon a dielectric 917. The surface layer may be such that the aqueous phase, for example, is preferred to wet across the surface as shown by the contact of exemplary aqueous fluid layer 915 across it. Underlying the dielectric 917 may be electrodes 918. The fluid layers may be contacted by another electrode 914. When an electro potential is applied across the electrodes 918 and 914 the surface free energy at the surface of the surface layer 916 which is in the vicinity of electrodes 918 may change to favor wetting by the oil type layer (which may be considered an oil type wetting characteristic). This condition may be depicted at 920.

If the electrodes are defined such that the nanostructure containing liquid when localized into smaller regions such as the case for liquid 914 in the 920 case, then the nanospheres are concentrated into features that may assume the nanosurface type designs as shown in the inset at 920. These shapes would occur with concentrated nanometallic structures comprised of nanospheres 930 or nanorods 935, which may interact with light in similar fashions to the Metasurface components described previously. The nanospheres or nanorods with attached surface molecules may be formulated to be a single size component within the mixture of size ranging from commercially available 2 nm-250 nm sphere sizes from Discovery Scientific Inc. Alternatively a combination of different sizes may also be used. The optical properties of the fluids may be altered depending on the size of sphere used or the combination of various sizes. As well the ligands could play roles in interacting with the optical properties by determining the closest spacing between nanospheres in the liquid.

In some embodiments the side structure 911 may be designed to surround individual Metasurface elements. In other embodiments, multiple elements may be located within each isolated surface structure. The design of the electrode locations 918, or missing electrode locations, may be made such that the individual elements are spaced at roughly 250 nm or more apart. The relative surface area of the designed features 918 in these individual isolated cells may determine the relative amounts of the two immiscible fluids for containment of the design element of one fluid region when the EWOD effect causes the definition of Metasurface elements.

Figure 10:
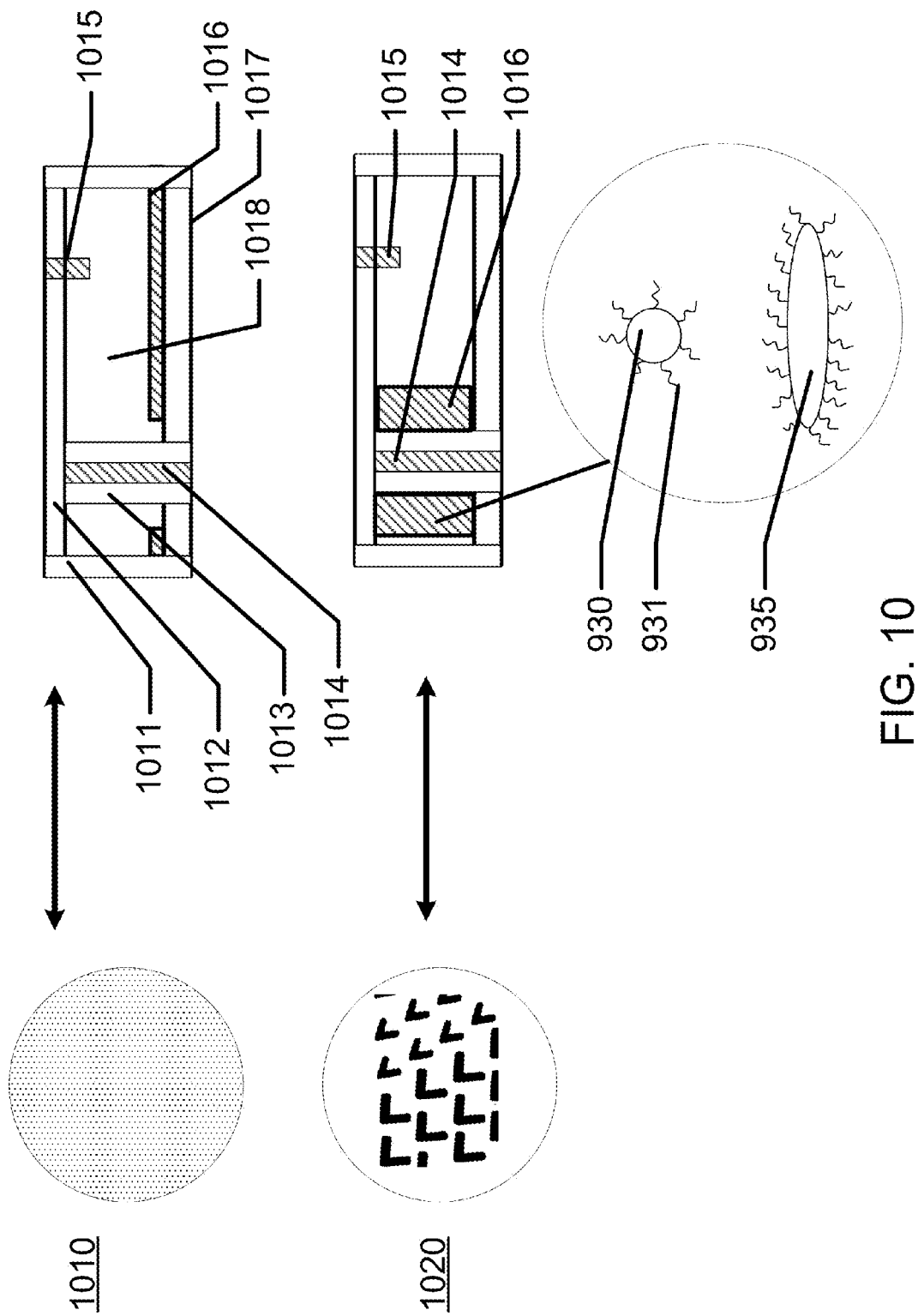
FIG. 10 Illustrates an alternative exemplary active ophthalmic device with structures that introduce Metasurface elements upon activation.

Proceeding to FIG. 10, an alternative embodiment to that in FIG. 9 may be found. Operating in a similar manner with Electrowetting as a means of defining active Metasurface elements, the embodiment in FIG. 10, builds up the layer with nanostructured devices along the sidewall of an electrode. At item 1010 the condition where the nanostructure containing liquid layer is located along the bottom of a small cell. The cell has similar structural features to that in embodiment 900. Item 1011 may be sidewalls containing the micro-fluidic cell. A top of the cell may be item 1012. Item 1014 may be an electrode formed in the desired shape of a nanosurface element. Item 1013 may be a dielectric film formed on the sidewall of the electrode that has the desired wetting properties on its side. Item 1015 may be an electrode that penetrates through the top of the cell. Item 1016 may be the fluid layer containing the solvated nanospheres and item 1018 may be the other fluid layer. The layer 1016 may have the similar metallic nanospheres 930 and nanorods 935, which may have attached ligand molecules 931 to define the surface free energy of the nanostructure and therefore which liquid type it would prefer to be solvated within.

When an electric field is applied across electrode 1015 and electrode 1016, this applied potential may change the surface free energy of the sidewall region of item 1016 causing the fluid layer 1016 to move along the sidewall region as shown in the depiction related to 1020. The accumulation of the fluid in the region may form the Metasurface structures as shown in item 1020. Again, the application of voltage across the cells may generate an active nanostructure pattern that may have the modeled optical effects. In some embodiments, the application of the voltage may be controlled by the electronics contained within an insert structure that also contains energization elements.

The resulting Metasurface structures that are created in the embodiment of item 1020 where they are located in the proximity of the metal electrode may have altered optical interaction because the structure of metal nanostructures with a dielectric and a second metal structure may create nanostructures with couple more strongly with the magnetic field of the electromagnetic radiation. This may create additional wavelength based resonances based on parameters such as the thickness of the dielectric film. This may create another dimension for the modeling of the nanosurface structures incorporated into such embodiments.

Methods

Figure 11:
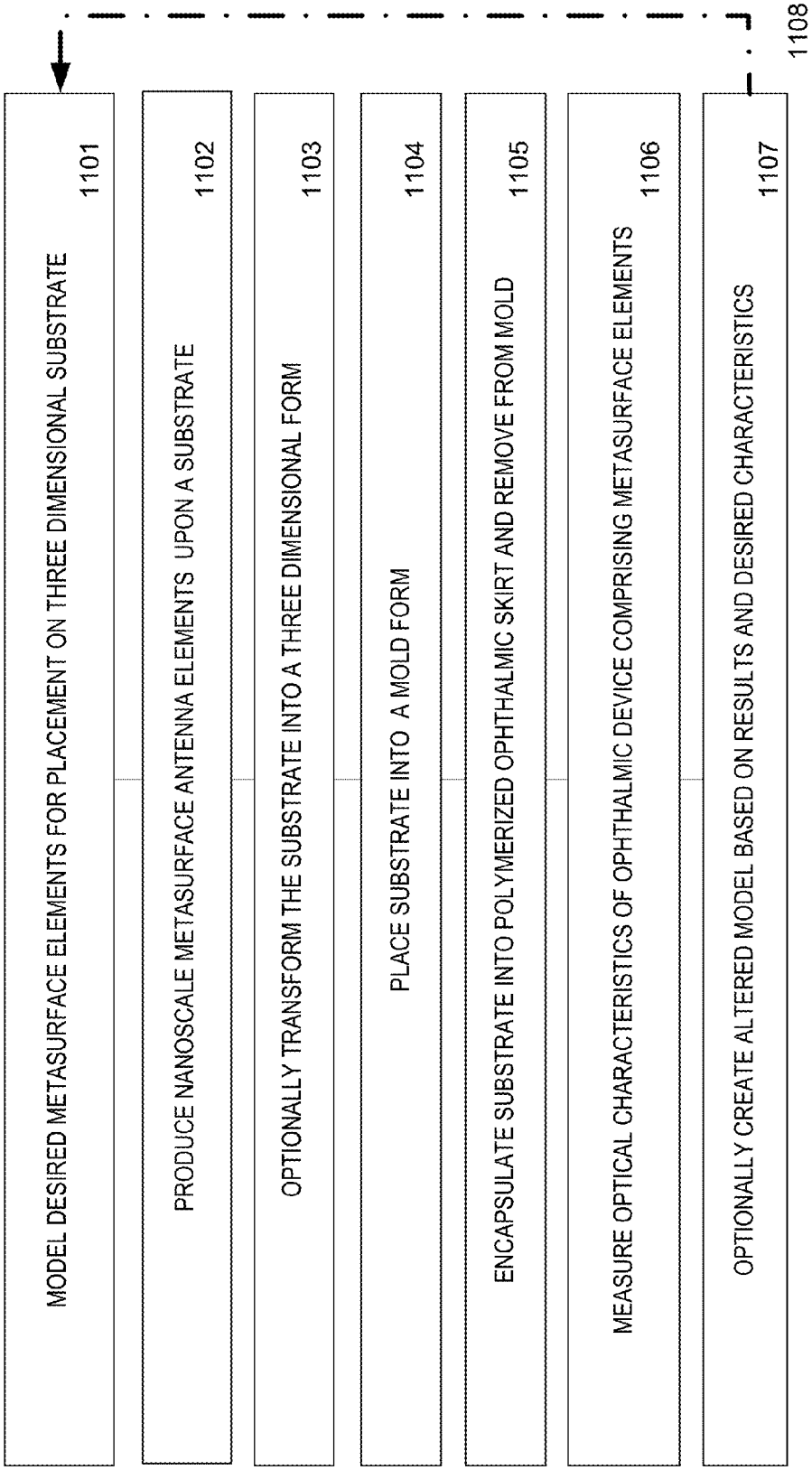
FIG. 11 Illustrates exemplary methods for designing and forming Ophthalmic devices with incorporated static Metasurface elements.

Proceeding to FIG. 11, item 1100, exemplary methods of designing and forming ophthalmic devices which include Metasurface elements may be found. At 1101 a model for an ophthalmic device may be formed. The model may comprise a three dimensional substrate form which may have at least two important aspects. First, the substrate form will typically define a shape of a conventional ophthalmic device which may understood optical properties, which also may be represented as point based phase characteristics imparted to incident light. Second, upon the shape or within the shape a network or array of three dimensionally deployed Nanoscaled metallic elements may be layed out. The system may be used by sophisticated modeling systems that model the wavefront characteristics of the optic elements and the nature of the electromagnetic interaction with the Nanoscale Metasurface elements. In other simplified estimates, the model may be broken down into a standard device lens characteristics and a superimposed Metasurface lens which may be estimated to function as a flat Metasurface lens. Regardless of the modeling approach, desired ophthalmic parameters may be fed into the modeling system along with empirical results as appropriate to generate the design aspect of both the substrate shape as well as the individual nanosurface element designs across that shape.

Proceeding to 1102, the model information may be used to fabricate Nanoscale Metasurface antenna elements upon a substrate. In a non-limiting example, this process may first involve placing Metasurface elements upon a flat substrate and then forming the substrate into a desired three dimensional shape. For example, the forming of the flat substrate may be carried out by thermoforming. In order to place the Metasurface elements there may be numerous methods that can yield the desired result. A thermoformable substrate may be coated with a thin film of chemical resist as may be used in the semiconductor industry. Then, for example, a nanoimprint lithography substrate may be used to impress into the photoresist the pattern desired for the Metasurface elements. The nanoimprint substrate may be as large as the desired ophthalmic substrate or alternatively it may contain multiple versions of the desired ophthalmic substrate pattern. In some embodiments it may be possible to step the nanoimprint substrate multiple times across the ophthalmic substrate to transfer the appropriate pattern.

Again, as a non-limiting example, recesses into the thermoformable substrates may be etched by either a chemical etch or a reactive ion etching technique. A film of metal, typically comprising Gold, silver, platinum or copper or other metallic component or alloy may be deposited upon the substrate with etched features and photoresist. A lift-off process may next remove metal and photoresist leaving a pattern of nanostructured features. Chemical cleans and physical polishing steps may be useful to remove material remaining of the photoresist or metal layer.

At 1103, the resulting substrate may be transformed into a three dimensionally shaped feature. In some embodiments this may be performed by thermoforming the substrate. The resulting three dimensional shape may become a part of an insert or may be an insert in its own right. Next at 1104, an insert with the Nanoscale metallic features may be placed into a mold form. The insert, at 1105, may then be surrounded by ophthalmic material which may be called reactive mixture and encapsulated as ophthalmic material may be polymerized and shaped with the mold around the insert. When removed from the mold a form of an ophthalmic device may be obtained. At 1106, the resulting ophthalmic device may be measured for its optical characteristics for example by a wave front aberrometer. Results from the measurement may be used to determine if the device thus formed is acceptable. Alternatively, at 1107 an alternative model may be formed by adjusting parameters in the modeling system based on the measured results. At 1108, these adjusted parameters and modeling characteristics may be feed back for refinement of the lens design.

Figure 12:
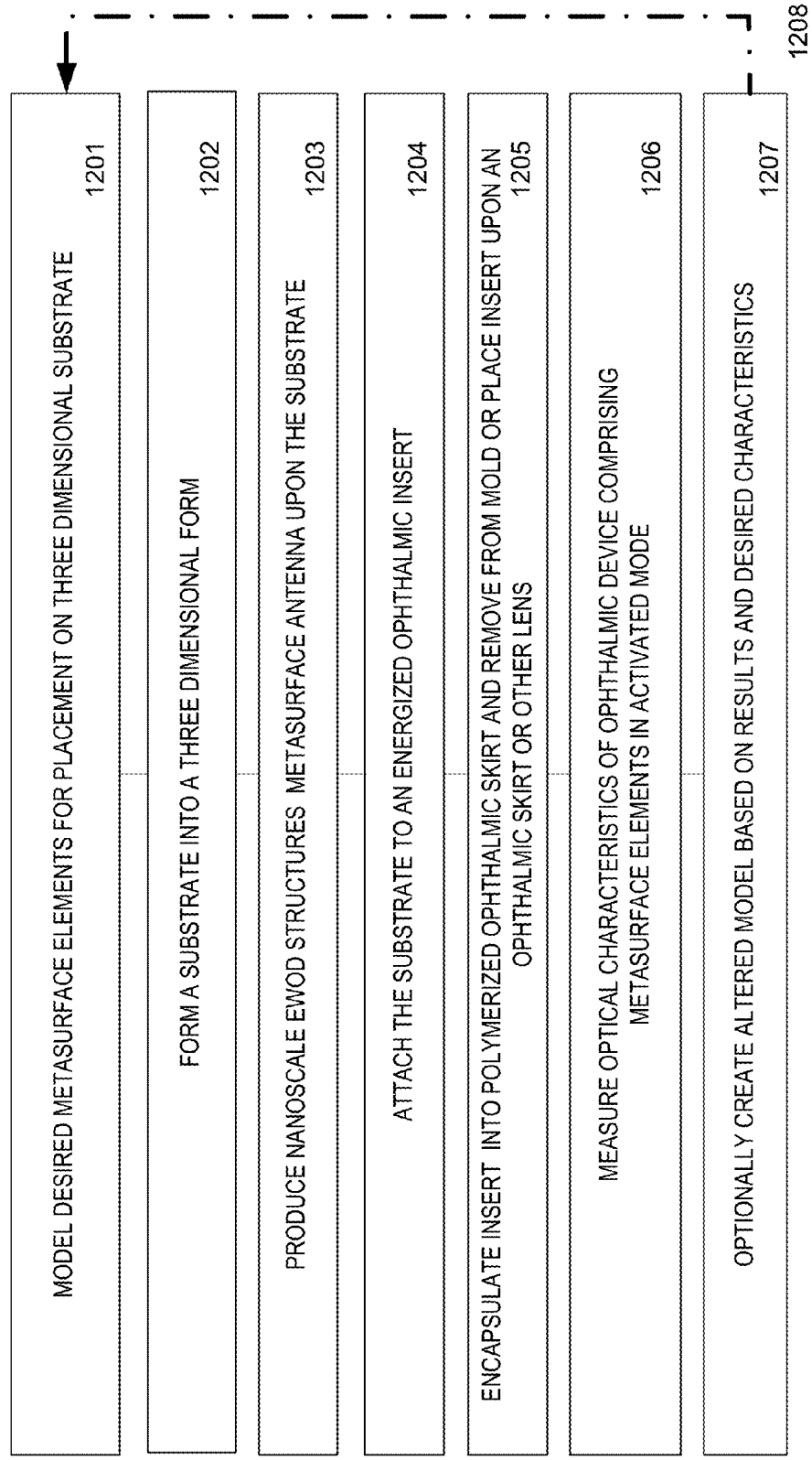
FIG. 12 Illustrates exemplary methods for designing and forming Ophthalmic devices with incorporated dynamic Metasurface elements.

Proceeding to FIG. 12, item 1200, exemplary methods of designing and forming ophthalmic devices which include active Metasurface elements may be found. The flow is similar to that discussed in reference to FIG. 11. At 1201 a model for an ophthalmic device may be formed. The model may comprise a three dimensional substrate form which may have at least two important aspects. First, the substrate form will typically define a shape of a conventional ophthalmic device which may understood optical properties, which also may be represented as point based phase characteristics imparted to incident light. Second, upon the shape or within the shape a network or array of three dimensionally deployed Nanoscale forming features may be laid out. As discussed in previous sections these forming features may cause Metasurface elements to form under the action of electric potentials. The resulting designed system may be used by sophisticated modeling systems that model the wavefront characteristics of the optic elements and the nature of the electromagnetic interaction with the Nanoscale Metasurface elements that would form actively. In other simplified estimates, the model may be broken down into a standard device lens characteristics and a superimposed Metasurface lens which may be estimated to function as a flat Metasurface lens and the complex active elements that may be collections of nanoparticles in a suspension in a fluid may be estimated as solid metallic features. Regardless of the modeling approach, desired ophthalmic parameters may be fed into the modeling system along with empirical results as appropriate to generate the design aspect of both the substrate shape as well as the individual nanosurface element designs across that shape.

Proceeding to 1202, the model information may be used to fabricate Nanoscale Metasurface antenna forming elements upon a substrate. In a non-limiting example, this process may first involve placing Metasurface controlling elements upon a flat substrate and then forming the substrate into a desired three dimensional shape. For example, the forming of the flat substrate may be carried out by thermoforming. In order to place the Metasurface controlling elements there may be numerous methods that can yield the desired result. A thermoformable substrate may be coated with a thin film of chemical resist as may be used in the semiconductor industry. Then, for example, a nanoimprint lithography substrate may be used to impress into the photoresist the pattern desired for the Metasurface elements. The nanoimprint substrate may be as large as the desired ophthalmic substrate or alternatively it may contain multiple versions of the desired ophthalmic substrate pattern. In some embodiments it may be possible to step the nanoimprint substrate multiple times across the ophthalmic substrate to transfer the appropriate pattern.

As a non-limiting example a film of metal, typically comprising Gold, silver, platinum or copper or other metallic component or alloy may be deposited upon the substrate with imprinted photoresist. A lift-off process may next remove metal and photoresist leaving a pattern of nanostructured metallic features. Chemical cleans and physical polishing steps may be useful to remove material remaining. A dielectric film may be deposited upon the substrate, covering the metallic features and the regions lacking metallic features. Some of the metallic features may be used as electrodes for the EWOD cells to be built in other cases they may be used to create the walls that surround each EWOD cell. The deposited dielectric film may be treated to condition its surface free energy. In a next step, the EWOD fluids may be added to the plurality of cells created across the substrate. Next, a layer comprising the top of the EWOD cells may be placed upon the growing substrate structure. Electrical interconnects may have already been placed upon the top layer structure for electrical connection.

At 1203, the resulting substrate structure may be transformed into a three dimensionally shaped structure. In some embodiments this may be performed by thermoforming the substrate. The resulting three dimensional shape may become a part of an insert or may be an insert in its own right. It may be electrically connected to other components within the insert as well. Next at 1204, an insert with the Nanoscale metallic controlling features may be placed into a mold form. The insert, at 1205, may then be surrounded by ophthalmic material, which may be called reactive mixture, and encapsulated as ophthalmic material may be polymerized and shaped with the mold around the insert. When removed from the mold a form of an ophthalmic device may be obtained. At 1206, the resulting ophthalmic device may be measured for its optical characteristics for example by a wave front aberrometer. The control electronics in the energized insert within the ophthalmic device may allow for a test mode activation of the ophthalmic device and both states with Metasurface elements and without may be tested. Results from the measurement may be used to determine if the device thus formed is acceptable. Alternatively, at 1207 an alternative model may be formed by adjusting parameters in the modeling system based on the measured results. At 1208, these adjusted parameters and modeling characteristics may be feed back for refinement of the lens design.

Figure 13:
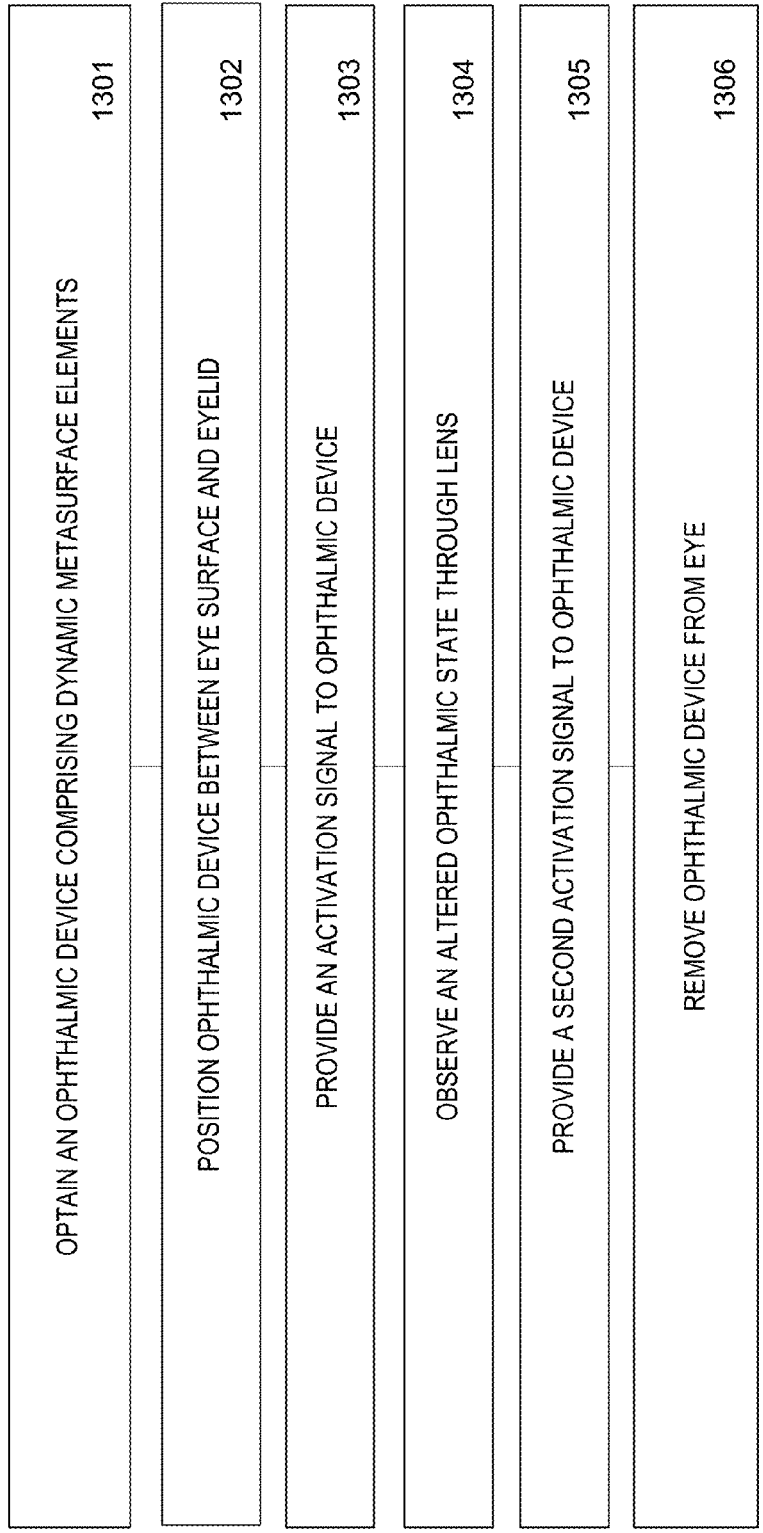
FIG. 13 Illustrates exemplary methods for utilizing Ophthalmic devices with incorporated dynamic Metasurface elements.

There may also be methods for using an Ophthalmic device which has an energized insert comprising Metasurface forming elements. In some embodiments, the Ophthalmic device may have two operational states related to the Metasurface forming elements. In a first state when the Metasurface elements are activated, the lens may have a first effective focal characteristic and in the other state when the Metasurface elements are deactivated it may have a second focal characteristic. Thus, proceeding to FIG. 13, item 1300 a method for utilizing such an active Ophthalmic device may be found. At 1301, an ophthalmic device with active Metasurface elements may be obtained. When the device is a contact lens embodiment, it may be placed in the user's eye region at 1302. When settled in place, the user will observe the lens through his eye to have a certain optical quality and characteristic. Next at 1303 the user may provide an activation signal of some kind. This may entail signals that the user may directly control, such as for example intentionally blinking his eyelids in some fashion. Alternatively, wireless communication devices may be controlled by the user to provide a signal. The signal when received by the ophthalmic device may cause it to shift states. At 1304, the user may then observe the result of the state shift through the ophthalmic device and recognize an altered optical quality and characteristic. In some embodiments, the user may provide a second activation signal at 1305 which may restore the active Ophthalmic device to the previous state it occupied prior to step 1303. The device may be removed from the eye at step 1306.

The invention claimed is:

1. A method for forming a rigid insert for an ophthalmic device comprising:
    depositing nanoscale metallic features onto a substrate to form a metasurface, wherein the nanoscale metallic features have a surface area of less than or equal to 10,000 nm²;
    theroforming the substrate with the nanoscale metallic features into a three-dimensional form; and
    securing the three-dimensionally thermoformed substrate to an insert to form the rigid insert.

2. The method according to claim 1 additionally comprising:
    designing the shapes and sizes of the nanoscale metallic features on a computerized system comprising modeling software.

3. The method according to claim 2 additionally comprising:
    placing the rigid insert within a mold;
    surrounding the rigid insert with a reactive mixture in the mold; and
    polymerizing the reactive mixture to form an ophthalmic device.

4. The method according to claim 3 additionally comprising:
    measuring optical characteristics of the ophthalmic device.

5. The method according to claim 4 additionally comprising:
    utilizing results obtained from the measuring of the optical characteristics of the ophthalmic device to adjust a design process for the rigid insert.

6. The method according to claim 5 wherein parameters inputted into the modeling software come from ophthalmic measurements performed upon a patient.

7. The method according to claim 1 wherein:
    the nanoscale metallic features are arranged in a periodic pattern, the periodic pattern having a periodicity of less than or equal to 700 nm.

8. The method according to claim 7, wherein the periodic pattern has a periodicity of greater than or equal to 200 nm.

9. The method according to claim 1, wherein the metasurface is configured to provide vision enhancement to an eye of a patient.

10. The method according to claim 9, wherein the metasurface alters the optical properties of the rigid insert in a non-radially symmetric manner.

11. A method for forming an opthalmic device utilizing the method according to claim 1 and additionally comprising:
    placing the rigid insert within a mold;
    surrounding the rigid insert with a reactive mixture in the mold; and
    polymerizing the reactive mixture.

12. A method for forming a rigid insert for an opthalmic device comprising:
    depositing nanoscale metallic features onto a three-dimensionally thermoformed substrate to form a metasurface, wherein the nanoscale metallic features have a surface area of less than or equal to 10,000 nm²; and
    securing the three-dimensionally thermoformed substrate to an insert to form the rigid insert.

13. The method according to claim 12, wherein the nanoscale metallic features are arranged in a periodic pattern, the periodic pattern having a periodicity of less than or equal to 700 nm.

14. The method according to claim 13, wherein the periodic pattern has a periodicity greater than or equal to 200 nm.

15. The method according to claim 12, wherein the metasurface is configured to provide vision enhancement to an eye of a patient.

16. The method according to claim 15, wherein the metasurface alters the optical properties of the rigid insert in a non-radially symmetric manner.

17. A method for forming an opthalmic device utilizing the method according to claim 12 and additionally comprising:
    placing the rigid insert within a mold;
    surrounding the rigid insert with a reactive mixture in the mold; and
    polymerizing the reactive mixture.

* * * * *